(12) United States Patent
Won

(10) Patent No.: US 9,839,707 B2
(45) Date of Patent: Dec. 12, 2017

(54) SMALL HOUSEHOLD GOODS SANITIZING APPARATUS

(71) Applicant: Haion Won, Basking Ridge, NJ (US)

(72) Inventor: Haion Won, Basking Ridge, NJ (US)

( * ) Notice: Subject to any disclaimer, the term of this patent is extended or adjusted under 35 U.S.C. 154(b) by 0 days.

(21) Appl. No.: 14/321,272

(22) Filed: Jul. 1, 2014

(65) Prior Publication Data

US 2016/0000950 A1  Jan. 7, 2016

(51) Int. Cl.
*A61L 2/10* (2006.01)

(52) U.S. Cl.
CPC ...................... *A61L 2/10* (2013.01)

(58) Field of Classification Search
CPC .... A61L 2/10; A61L 2202/11; A61L 2202/16; A61L 2202/23; A23L 3/28
See application file for complete search history.

(56) References Cited

U.S. PATENT DOCUMENTS

| | | | | |
|---|---|---|---|---|
| 4,210,073 A * | 7/1980 | Weiss | .................. | A47J 36/2483 126/281 |
| 5,439,128 A * | 8/1995 | Fishman | .................... | A45F 3/20 206/218 |
| 5,860,556 A * | 1/1999 | Robbins, III | ........ | B65D 1/0292 220/608 |
| 6,461,568 B1 * | 10/2002 | Eckhardt | .................... | A61L 2/10 250/455.11 |
| 7,654,402 B2 * | 2/2010 | Kusuma | ............... | B65D 21/086 220/666 |
| 8,193,515 B2 * | 6/2012 | Kreitenberg | .............. | A61L 2/10 250/455.11 |
| 8,964,405 B2 * | 2/2015 | La Porte | .................... | A61L 2/10 361/807 |
| 9,045,358 B2 * | 6/2015 | Greuel | ..................... | C02F 1/325 |
| 2008/0067418 A1 * | 3/2008 | Ross | ......................... | A61L 2/10 250/455.11 |
| 2008/0265179 A1 * | 10/2008 | Havens | ..................... | A61L 2/10 250/492.1 |
| 2010/0044582 A1 * | 2/2010 | Cooper | ..................... | A61L 2/10 250/455.11 |
| 2010/0200583 A1 * | 8/2010 | Curtin | ................. | B65D 43/0206 220/4.27 |
| 2010/0329924 A1 * | 12/2010 | Harris | ....................... | A61L 2/10 422/5 |
| 2011/0133649 A1 * | 6/2011 | Kreiner | .............. | H05B 33/0842 315/86 |
| 2012/0006995 A1 * | 1/2012 | Greuel | ..................... | C02F 1/325 250/373 |
| 2012/0051979 A1 * | 3/2012 | Clark | ......................... | A61L 2/10 422/186.3 |
| 2012/0068088 A1 * | 3/2012 | Durkin | ...................... | A61L 2/10 250/492.1 |
| 2012/0074334 A1 * | 3/2012 | Milligan | .................... | A61L 2/10 250/455.11 |
| 2013/0004367 A1 * | 1/2013 | Roberts | .................... | A61L 2/10 422/24 |

(Continued)

*Primary Examiner* — Wyatt Stoffa
(74) *Attorney, Agent, or Firm* — The Song Law Firm

(57) ABSTRACT

An enclosure has a bottom open ended portion that serves to cover any of a variety of household goods. The top surface to the enclosure has a circuit formed of a switch, an ultraviolet (UV) light or lamp and battery to power the UV light or lamp. The UV light projects downward onto the enclosed household goods to sanitize the enclosed goods.

7 Claims, 8 Drawing Sheets

Before Collapsed

(56) References Cited

U.S. PATENT DOCUMENTS

| | | | | |
|---|---|---|---|---|
| 2013/0319915 | A1* | 12/2013 | Gellibolian | C02F 1/002 210/87 |
| 2014/0060095 | A1* | 3/2014 | Shur | A61L 2/10 62/129 |
| 2014/0127077 | A1* | 5/2014 | Rock | A61L 2/0088 422/28 |
| 2014/0175280 | A1* | 6/2014 | Tantillo | A63H 33/006 250/338.1 |
| 2014/0319375 | A1* | 10/2014 | Nelson | A61L 2/025 250/455.11 |
| 2014/0356229 | A1* | 12/2014 | Farren | A23L 3/28 422/24 |
| 2014/0363335 | A1* | 12/2014 | Dam | A61L 2/10 422/24 |
| 2015/0069270 | A1* | 3/2015 | Shur | F25D 17/042 250/492.1 |
| 2015/0190537 | A1* | 7/2015 | Kerr | A61L 2/10 134/1 |

* cited by examiner

Front View

Before Collapsed

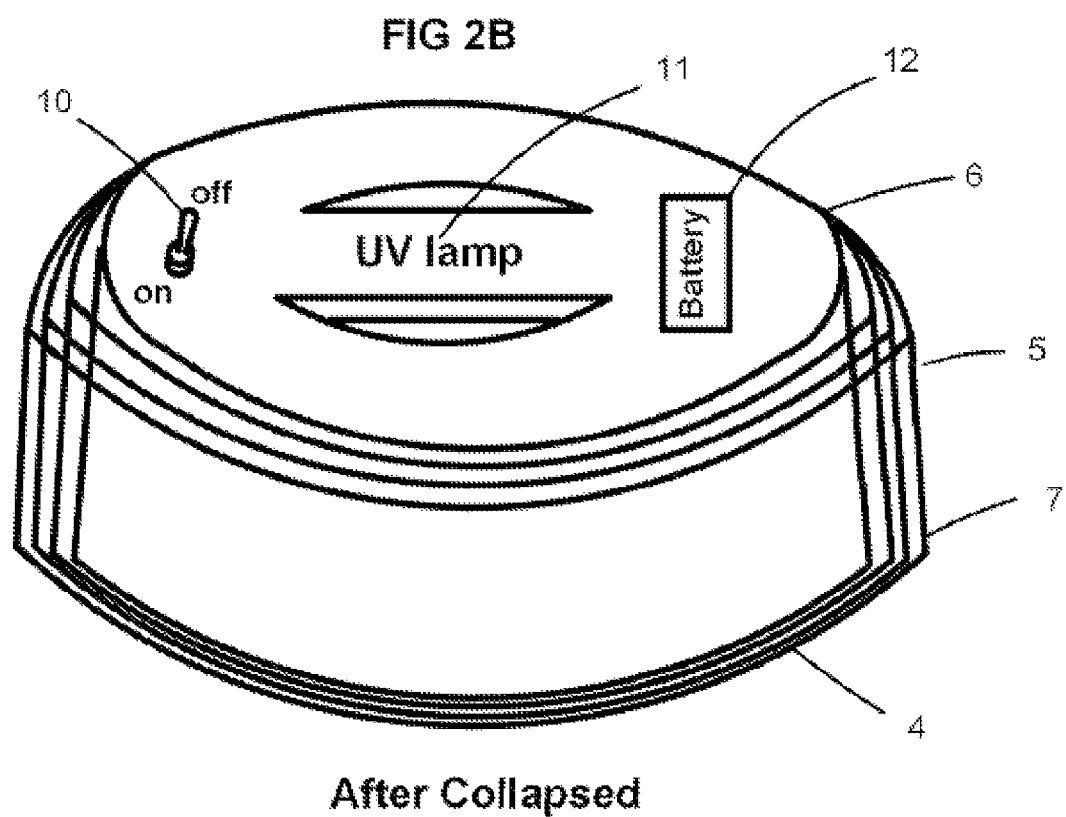

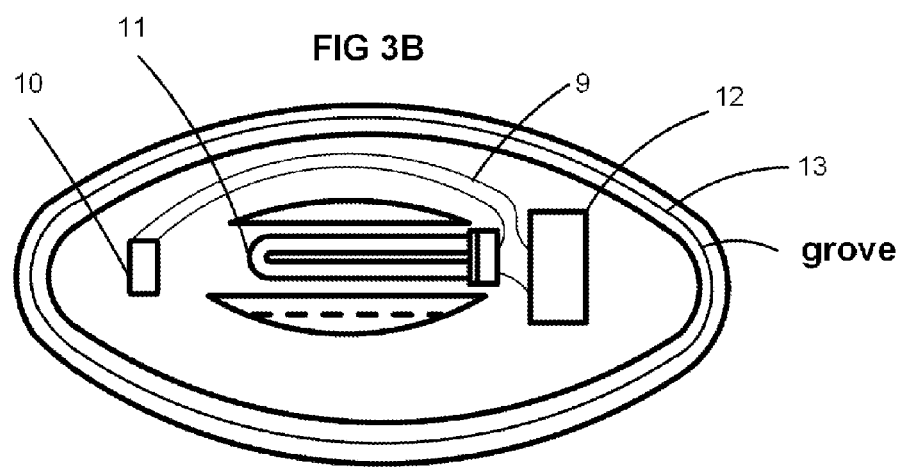
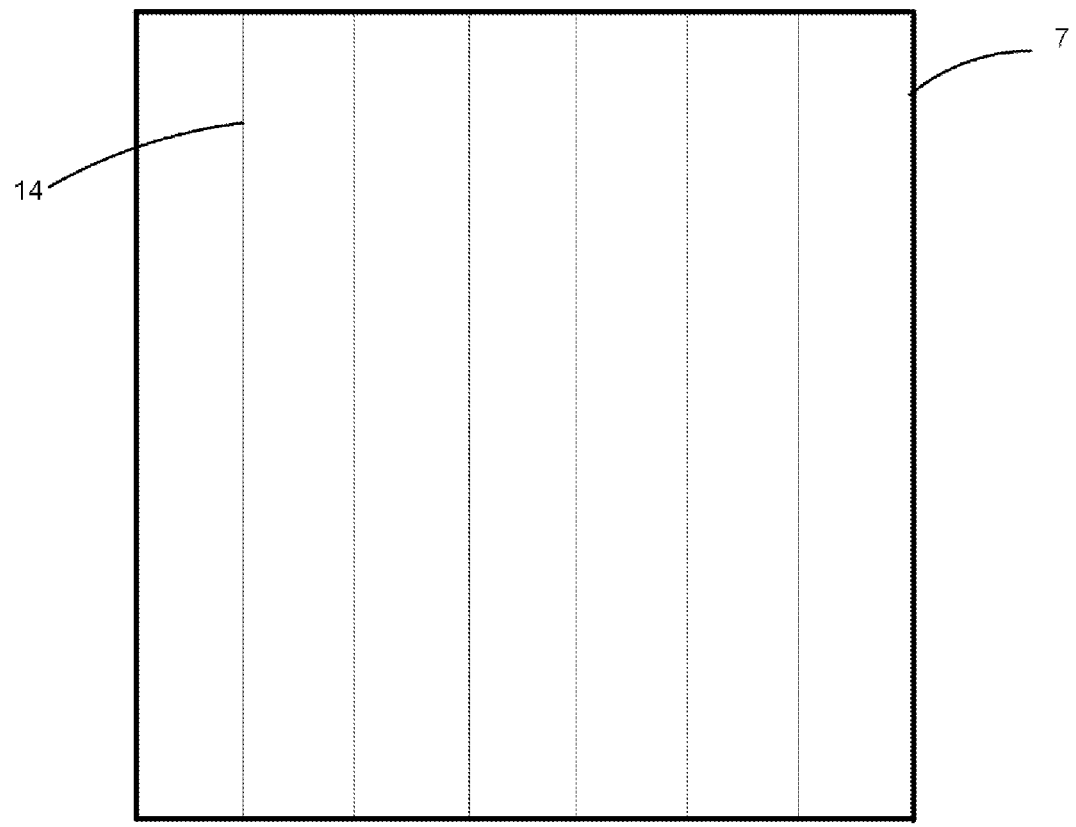

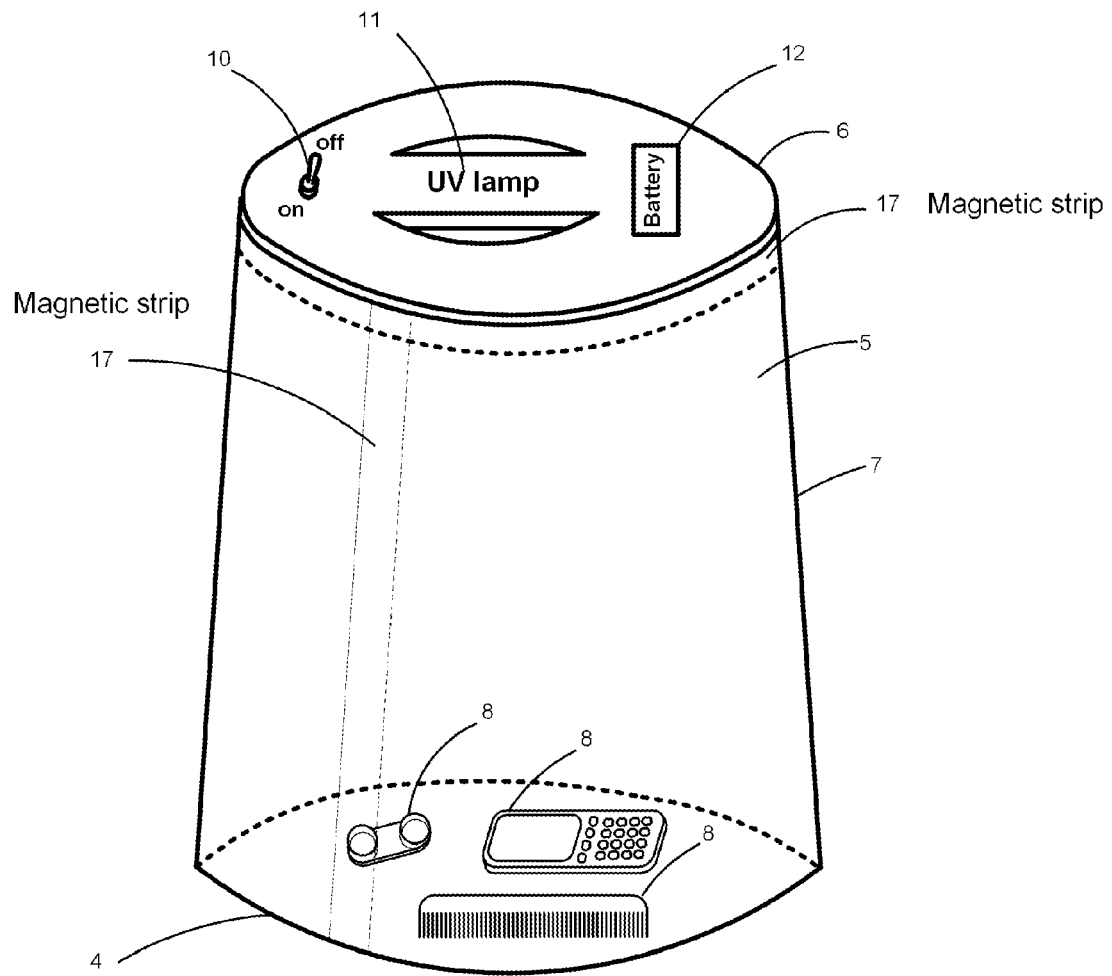

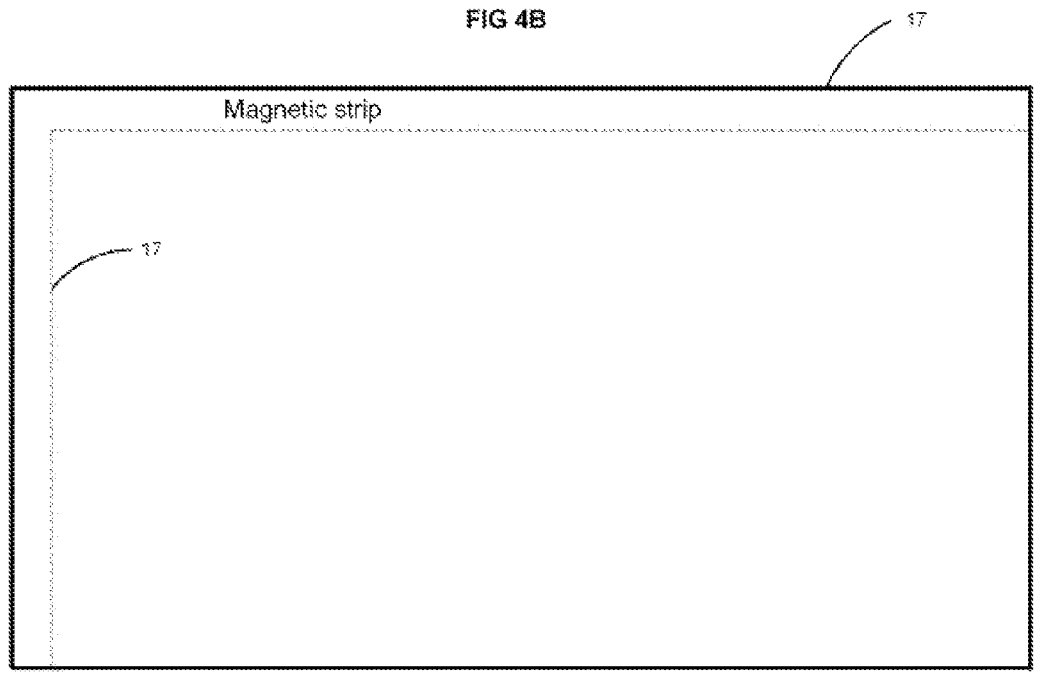

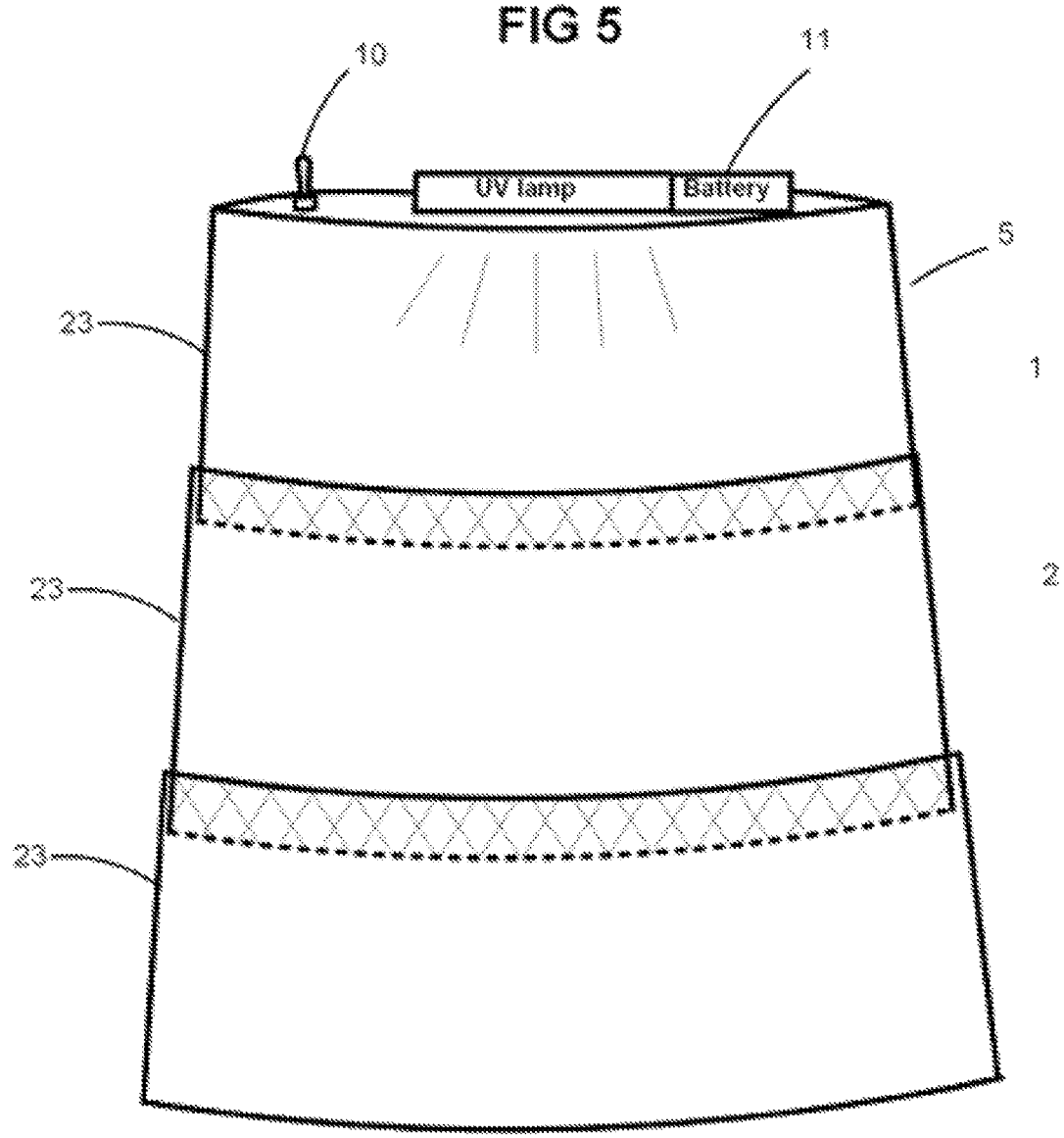

SMALL HOUSEHOLD GOODS SANITIZING APPARATUS

BACKGROUND

1. Field

The present invention relates to a small household goods sanitizing apparatus. In particular the present invention relates to an enclosure having a bottom open ended portion that serves to cover any of a variety of household goods in which the top surface to the enclosure has a circuit formed of a switch, an ultraviolet (UV) light or lamp and battery to power the UV light or lamp sot at the UV light projects downward onto the enclosed household goods to sanitize these goods.

2. The Related Art

Although items can be sanitized and stored away it would be desirable to have a simple, portable sanitizing device that can cover or be fitted over any good or goods.

SUMMARY

The present invention provides for a simple, portable enclosure that can sanitize goods, notably household goods, such as but not limited to tooth brushes, toys, forks, knives, spoons, cellular phones, scouring sponges. The enclosure can have any shape but preferably a conical or cylindrical shape. The present invention can be configured to fit over a kitchen sink, a bath tub or a shower sink.

BRIEF DESCRIPTION OF THE DRAWINGS

FIGS. 2A and 2B show perspective views of a second embodiment of the present invention in which:

FIG. 2A shows the present invention as a collapsible cup like enclosure in its extended or non-collapsed position and FIG. 2B shows the cup-like enclosure in its collapsed position;

FIGS. 3A and 3B show perspective views of a third embodiment of the present invention in which:

FIG. 3A shows the present invention formed with a slotted side wall that can bend and curve and be inserted into a preferably circumferential groove of the top portion containing the UV lamp, switch and battery and FIG. 3B shows the top portion with the groove and the slotted side wall separate from each other;

FIGS. 4A and 4B show perspective views of a fourth embodiment of the present invention in which:

FIG. 4A shows the present invention formed with a magnetic strip that encircles the circumference of the bottom edges of the top portion of the enclosure to connect with the top surface of the side wall of the enclosure to connect the top portion to the side wall and the magnetic strip connects to ends of the side walls together to form an enclosed side wall structure for the enclosure;

FIG. 4B shows the magnetic strip that attaches the sidewall ends together and the top of the side wall to the top portion of the enclosure; and FIG. 5 is another embodiment of the present invention in which the enclosure of the percent invention has rough exterior surfaces facing one another when the collapsible container enclosure is in its extended protracted position thereby increasing the friction between the collapsing rings of the enclosure.

DETAILED DESCRIPTION OF THE PREFERRED EMBODIMENTS

Figure 1:
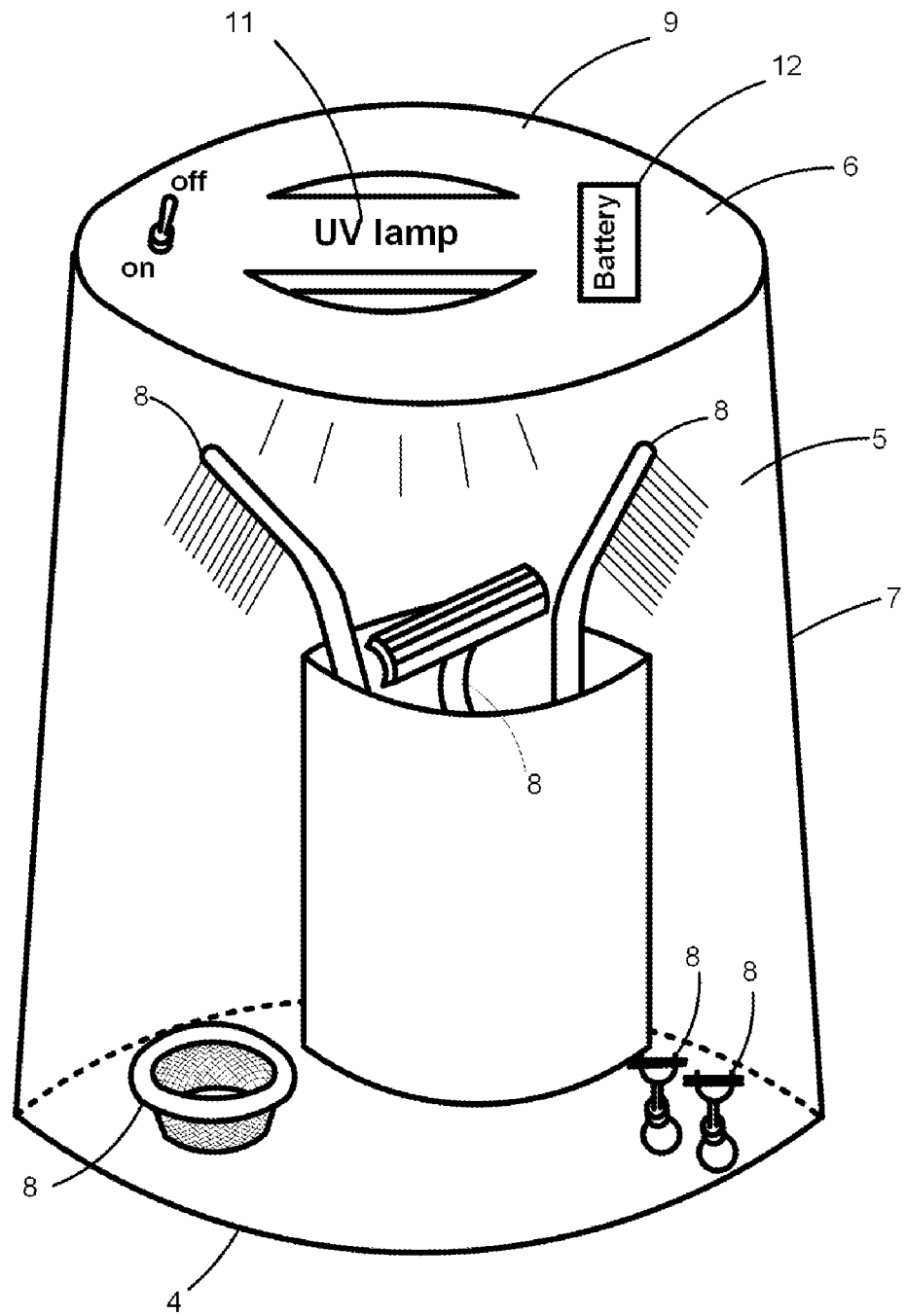
FIG. 1 shows a perspective view of first embodiment of the present invention.

Referring now to the drawings of FIGS. 1-5, FIG. 1 shows a first embodiment of the present invention of an enclosure 5, preferably conically shaped, having a top portion 6, a side wall 7 and an open ended bottom portion 4 that encircles and covers any of a variety of household goods 8 such as by way of non limiting illustrative example a tooth brush, a razor, small jewelry items such as earrings, a thimble. The list of goods 8 are veritably endless and can include toys, silverware, knives, forks and spoons (see FIG. 2A), scouring sponges (see FIG. 3A), combs and contact lenses cases (see FIG. 4B). The goods can be placed in a cup and stored within the enclosure 5 as shown in FIG. 1. The top portion 6 includes a simple electrical circuit 9 formed of a switch 10, an ultra violet (UV) lamp 11 and a battery 12 to power the UV lamp 11. The circuit is shown in wired form in the embodiment of FIG. 3B. The switch shown in FIG. 1A is a toggle switch however the present invention is not limited to this switch. The switch can be provided by way of illustrative non limiting example as a sliding switch or a button switch. The enclosure of FIG. 1 is preferably formed in one piece and can be manufactured of plastic, silicon or stainless steel or any other suitable material. The UV lamp 11 projects downward onto the enclosed household goods 8 housed within the side wall 7 of the enclosure 5 so as to sanitize these goods 8 with the UV lamp 11. The enclosure 5 can be placed onto any surface over which it will sanitize the goods 8 located thereon. With the present invention there is no need to open a door for the enclosure 5 to place the household goods 8 inside the enclosure 5. The enclosure 5 can be fitted over a kitchen sink, a bathtub or a shower sink or practically any intended location in to provide a sterilizing environment for goods 8.

Figure 2A:
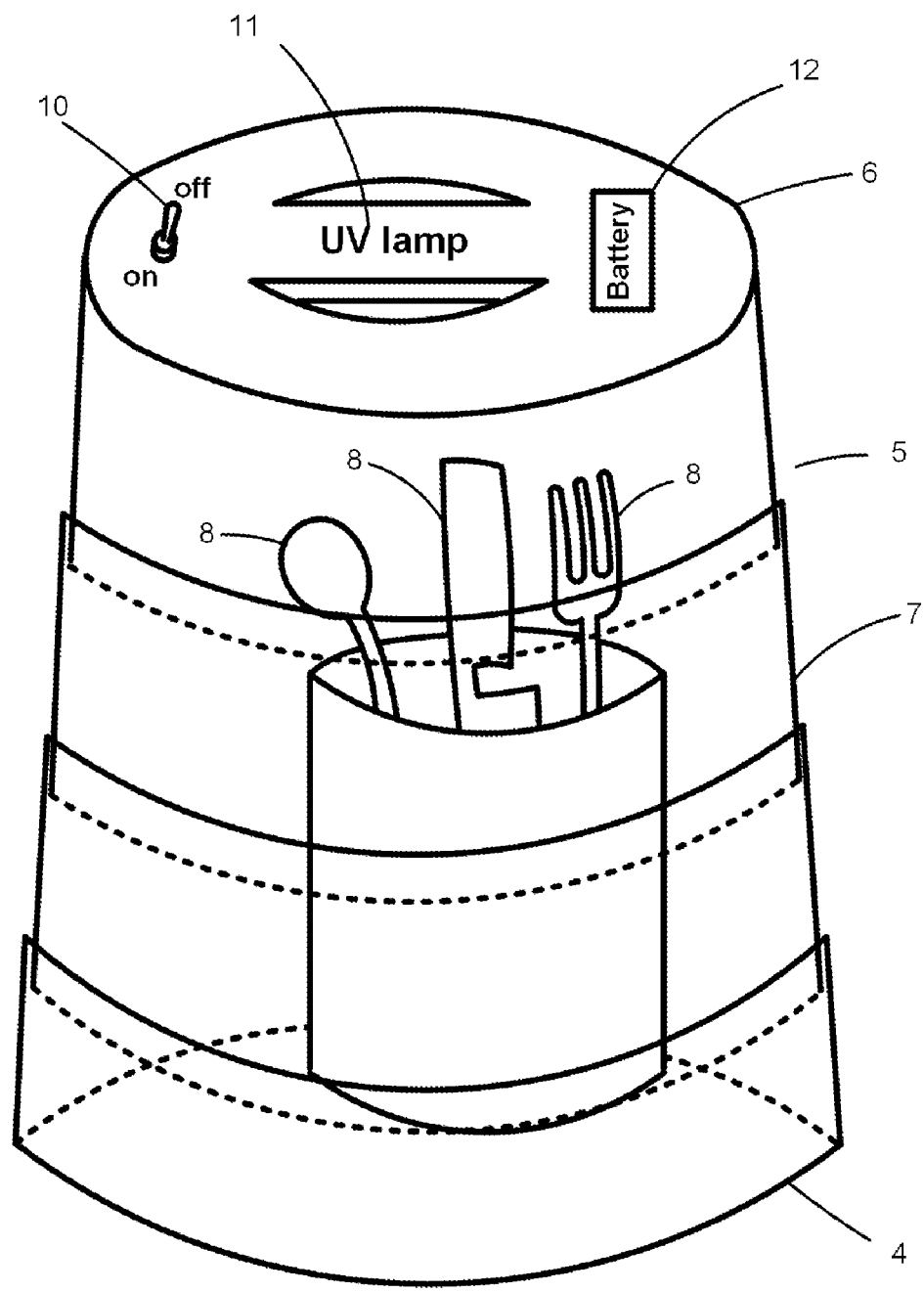

FIGS. 2A and 2B show a second embodiment of the present invention in which the enclosure 5 can be formed as a collapsible structure 5. The side wall 7 of the enclosure can be configured with telescoping sectional wall structure that can unfold to a full height as show in FIG. 2A or collapse or fold up with a top section collapsing into the next section below that and that next section collapsing or folding into the section below it and so on until it folds into the structure shown in FIG. 2B. This embodiment provides for an enclosure 5 that can be made smaller for storage, more portable, can reduce manufacturing cost and is easier to ship since it can be shipped in its collapsed state (FIG. 2B). The top surface and circuit is as described above with reference to FIG. 1.

Figure 3A:
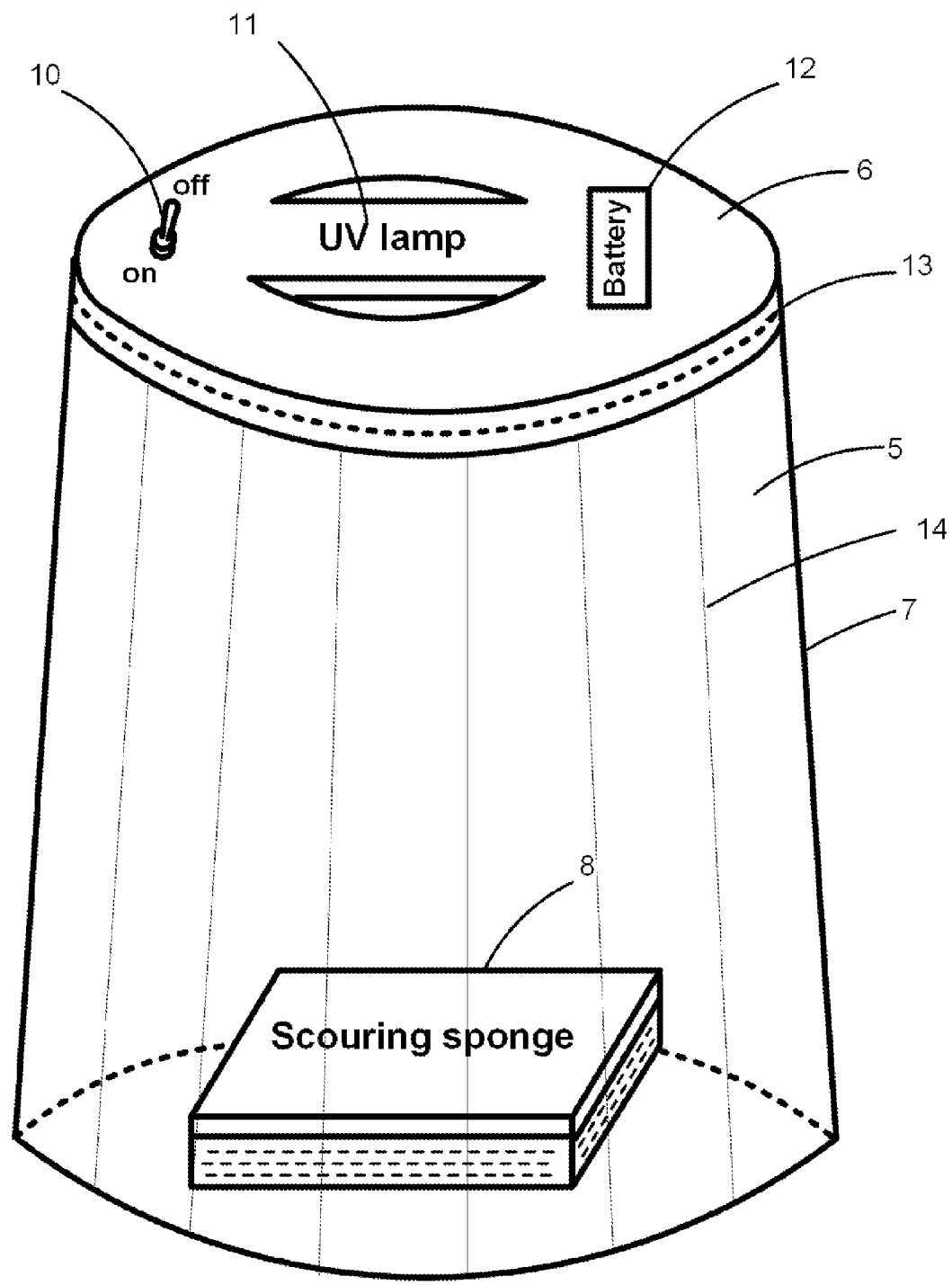

FIGS. 3A and 3B show a third embodiment of the present invention where the enclosure 5 has a side wall 7 that is formed with a slitted or slotted 14 side wall 7 that can bend and curve and be inserted into a preferably circumferential groove 13 of the top portion 6 containing the UV lamp 11, the switch 10 and the battery 12. FIG. 3B shows the top portion 6 with the groove 13 and the slotted 14 side wall 7, formed with slots 14, separate from each other. FIG. 3B shows the electrical circuit 9 connecting, with wiring, the switch 10, the UV lamp 11 and the battery 12 to form the circuit 9.

FIGS. 4A and 4B show a fourth embodiment of the present invention in which the present invention is formed with a magnetic strip 17 that encircles the circumference of the bottom edges of the top portion 6 of the enclosure to connect with the top surface of the side wall 7 of the enclosure 5 to connect the top portion 6 to the side wall 7 and the magnetic strip 17 connects to ends of the side wall 7 together to form an enclosed side wall 7 structure for the enclosure 5. FIG. 4B shows the magnetic strip 17 that attaches the sidewall 7 ends together and the top of the side wall 7 to the top portion 6 of the enclosure 5.

FIG. 5 is another embodiment of the present invention for a collapsible structure formed of rings sections 23 where when the collapsible container enclosure 5 formed with rings 23 where the top ring is slightly larger in diameter than the one below and the middle ring 23 section of the enclosure is slightly larger in diameter than the ring section below it but smaller than the ring section above it so that when the structure collapses the top ring encompasses the middle ring and the middle ring encompasses the bottom ring in which the enclosure 5 of the percent invention has rough exterior surfaces 21 facing one another when the collapsible container enclosure 5 formed with rings 23 where the top ring is slightly larger in diameter than the one below and the middle ring 23 section of the enclosure is slightly larger in diameter than the ring section below it but smaller than the ring section above it so that when the structure collapses the top ring encompasses the middle ring and the middle ring encompasses the bottom ring is in its extended protracted position thereby increasing the friction between the collapsing rings 23 of the enclosure 5. It is understood that the enclosure 5 of the present invention is not limited to any particular geometric shape or size. The rough surfaces 21 permit the collapsible container enclosure 5 to stand still firmly. The container 5 easily collapses with the application of just a little downward force.

While presently preferred embodiments have been described for purposes of the disclosure, numerous changes in the arrangement of method steps and apparatus parts can be made by those skilled in the art. Such changes are encompassed within the spirit of the invention as defined by the appended claims.

What is claimed:

1. A household goods sanitizing apparatus comprising: an enclosure, having a top portion, a side wall, and an open ended bottom portion that covers and encloses within said enclosure any of a variety of household goods, said top portion includes an electrical circuit formed of a switch, an ultraviolet (uv) lamp and a battery to power the uv lamp;
   wherein said uv lamp projects downward onto the enclosed household goods to sanitize the goods,
   wherein said side wall is formed as a telescoping collapsible cup like structure,
   and wherein the telescoping collapsible cup like structure extends to encircle the enclosed household goods.

2. The apparatus according to claim 1 wherein said enclosure is made of plastic material.

3. The apparatus according to claim 1 wherein said enclosure is made of silicon.

4. The apparatus according to claim 1 wherein said switch is a toggle switch.

5. The apparatus according to claim 1 wherein said switch is a sliding switch.

6. The apparatus according to claim 1 wherein said switch is a button switch.

7. The apparatus according to claim 1 wherein the household goods include cell phones, combs, brushes, tooth brushes, toys, contact lens cases, forks, knives, spoons, or razors.

\* \* \* \* \*